(12) United States Patent
Dunham et al.

(10) Patent No.: US 7,136,455 B2
(45) Date of Patent: Nov. 14, 2006

(54) ELECTRON EMITTER ASSEMBLY AND METHOD FOR ADJUSTING A SIZE OF ELECTRON BEAMS

(75) Inventors: Bruce Matthew Dunham, Mequon, WI (US); John Scott Price, Niskayuna, NY (US); Colin R. Wilson, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 59 days.

(21) Appl. No.: 10/904,286

(22) Filed: Nov. 2, 2004

(65) Prior Publication Data

US 2006/0098780 A1 May 11, 2006

(51) Int. Cl.
*H05G 2/00* (2006.01)

(52) U.S. Cl. ...................................... 378/119; 378/138

(58) Field of Classification Search ................ 378/119, 378/138, 136
See application file for complete search history.

(56) References Cited

U.S. PATENT DOCUMENTS

| | | | |
|---|---|---|---|
| 5,144,123 A * | 9/1992 | Malashanko | 250/214 VT |
| 5,680,431 A | 10/1997 | Pietras, III et al. | 378/119 |
| 6,181,765 B1 | 1/2001 | Sribar et al. | 378/10 |
| 6,385,292 B1 | 5/2002 | Dunham et al. | 378/122 |
| 6,516,048 B1 | 2/2003 | Mori | 378/119 |
| 2002/0085674 A1 * | 7/2002 | Price et al. | 378/122 |
| 2003/0095627 A1 * | 5/2003 | Anderton | 378/98.7 |

* cited by examiner

*Primary Examiner*—Edward J. Glick
*Assistant Examiner*—Chih-Cheng Glen Kao
(74) *Attorney, Agent, or Firm*—Cantor Colburn LLP

(57) ABSTRACT

An electron emitter assembly and a method for adjusting a size of electron beams are provided. The electron emitter assembly includes a laser configured to emit a first light beam. The electron emitter assembly further includes a lens assembly configured to receive the first light beam. The lens assembly is configured to adjust a size of the first light beam between a first predetermined size and a second predetermined size larger than the first predetermined size. The lens assembly emits the first light beam toward a photo-cathode. The photo-cathode is configured to emit a first electron beam having a third predetermined size when the first light beam having the first predetermined size contacts the photo-cathode. The photo-cathode is further configured to emit a second electron beam having a fourth predetermined size when the first light beam having the second predetermined size contacts the photo-cathode. The electron emitter assembly further includes an anode configured to receive the first and second electrons beams from the photo-cathode.

11 Claims, 15 Drawing Sheets

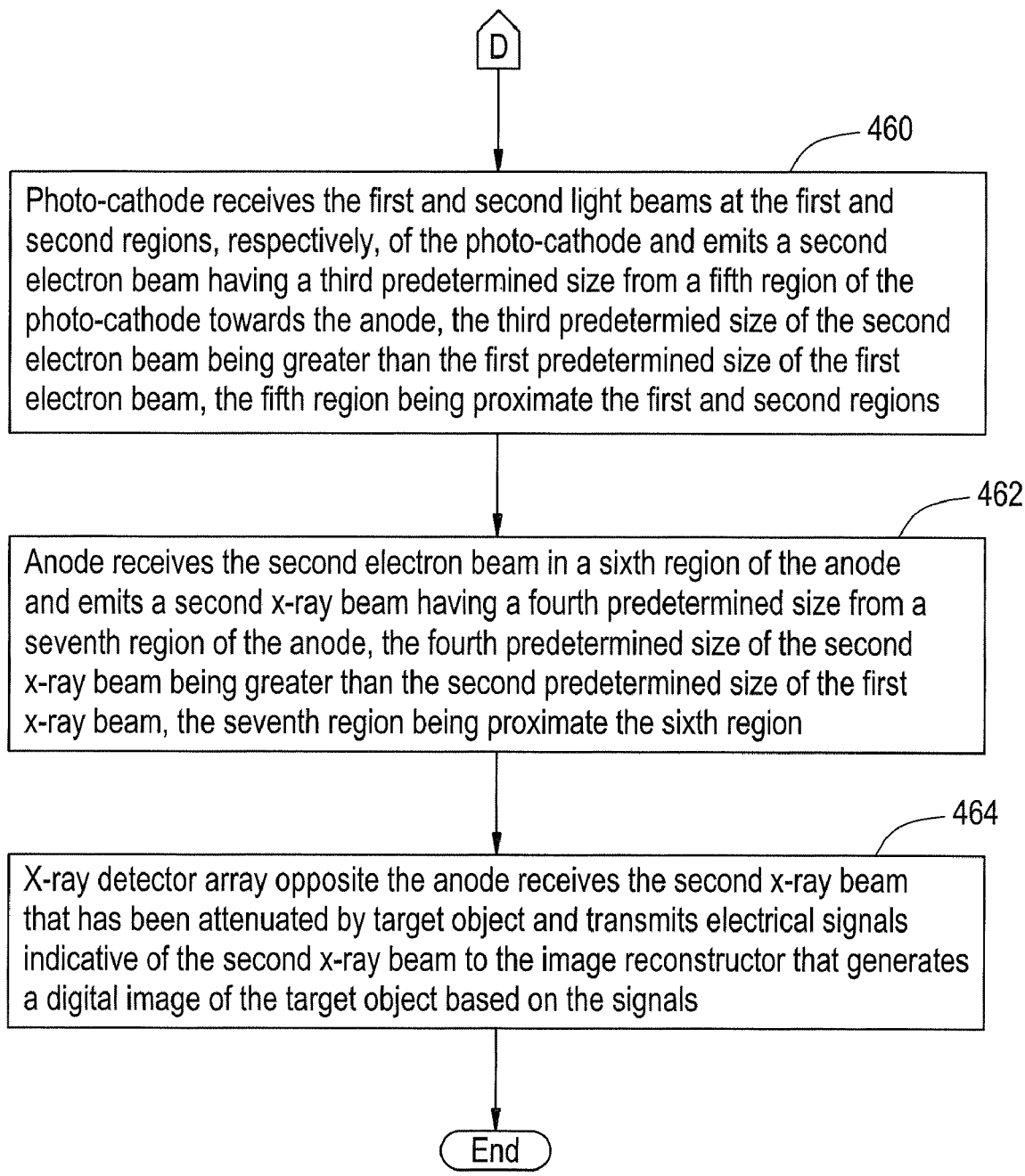

ELECTRON EMITTER ASSEMBLY AND METHOD FOR ADJUSTING A SIZE OF ELECTRON BEAMS

BACKGROUND OF THE INVENTION

In computed tomography (CT) imaging systems, an x-ray source device and a detector array have been utilized to generate images of an object. The x-ray source device includes an electron emitter device that emits an electron beam that contacts a substrate that subsequently emits an x-ray beam in response to the electron beam.

A disadvantage of the CT imaging system is that the electron emitter device can only adjust a size of the electron beam by utilizing first and second heating coils in the electron emitter device which can only adjust the beam size over a relatively large amount of time.

Accordingly, there is a need for an improved electron emitter device that can adjust the size of an electron beam during relatively small amounts of time without utilizing heating coils.

BRIEF DESCRIPTION OF THE INVENTION

An electron emitter assembly in accordance with exemplary embodiment is provided. The electron emitter assembly includes a laser configured to emit a first light beam. The electron emitter assembly further includes a lens assembly configured to receive the first light beam. The lens assembly is configured to adjust a size of the first light beam between a first predetermined size and a second predetermined size larger than the first predetermined size. The lens assembly emits the first light beam toward a photo-cathode. The photo-cathode is configured to emit a first electron beam having a third predetermined size when the first light beam having the first predetermined size contacts the photo-cathode. The photo-cathode is further configured to emit a second electron beam having a fourth predetermined size when the first light beam having the second predetermined size contacts the photo-cathode. The electron emitter assembly further includes an anode configured to receive the first and second electrons beams from the photo-cathode.

An electron emitter assembly in accordance with another exemplary embodiment is provided. The electron emitter assembly includes first and second laser diodes configured to emit first and second light beams, respectively, toward first and second regions of a photo-cathode, respectively. The photo-cathode is configured to emit a first electron beam having a first predetermined size when the photo-cathode receives the first light beam from the first laser diode. The photo-cathode is further configured to emit a second electron beam having a second predetermined size larger than the first predetermined size when the photo-cathode simultaneously receives the first and second light beams from the first and second laser diodes. The electron emitter assembly further includes an anode configured to receive the first and second electron beams from the photo-cathode.

A method for adjusting a size of an electron beam in accordance with another exemplary embodiment is provided. The method includes adjusting a size of a first light beam between a first predetermined size and a second predetermined size greater than the first predetermined size that is emitted toward a photo-cathode. The method further includes emitting a first electron beam having a third predetermined size from the photo-cathode toward an anode in response to the photo-cathode receiving the first light beam having the first predetermined size. The method further includes emitting a second electron beam having a fourth predetermined size greater than the third predetermined size from the photo-cathode toward the anode in response to the photo-cathode receiving the first light beam having the second predetermined size.

A method for adjusting a size of an electron beam in accordance with another exemplary embodiment is provided. The method includes emitting a first light beam having a first predetermined size towards a photo-cathode. The method further includes emitting a first electron beam having a second predetermined size from the photo-cathode toward an anode in response to the photo-cathode receiving the first light beam. The method further includes emitting both a second light beam having a third predetermined size and the first light beam toward the photo-cathode. The method further includes emitting a second electron beam having a fourth predetermined size from the photo-cathode toward the anode in response to the photo-cathode receiving the first and second light beams, the fourth predetermined size being greater than the second predetermined size.

BRIEF DESCRIPTION OF THE DRAWINGS

FIGS. 17–18 are flowcharts of a method for generating x-ray beams and varying a size of the x-ray beams utilizing the light emitting assembly and x-ray source assembly of FIG. 13 in accordance with another exemplary embodiment.

DETAILED DESCRIPTION OF THE INVENTION

Figure 1:
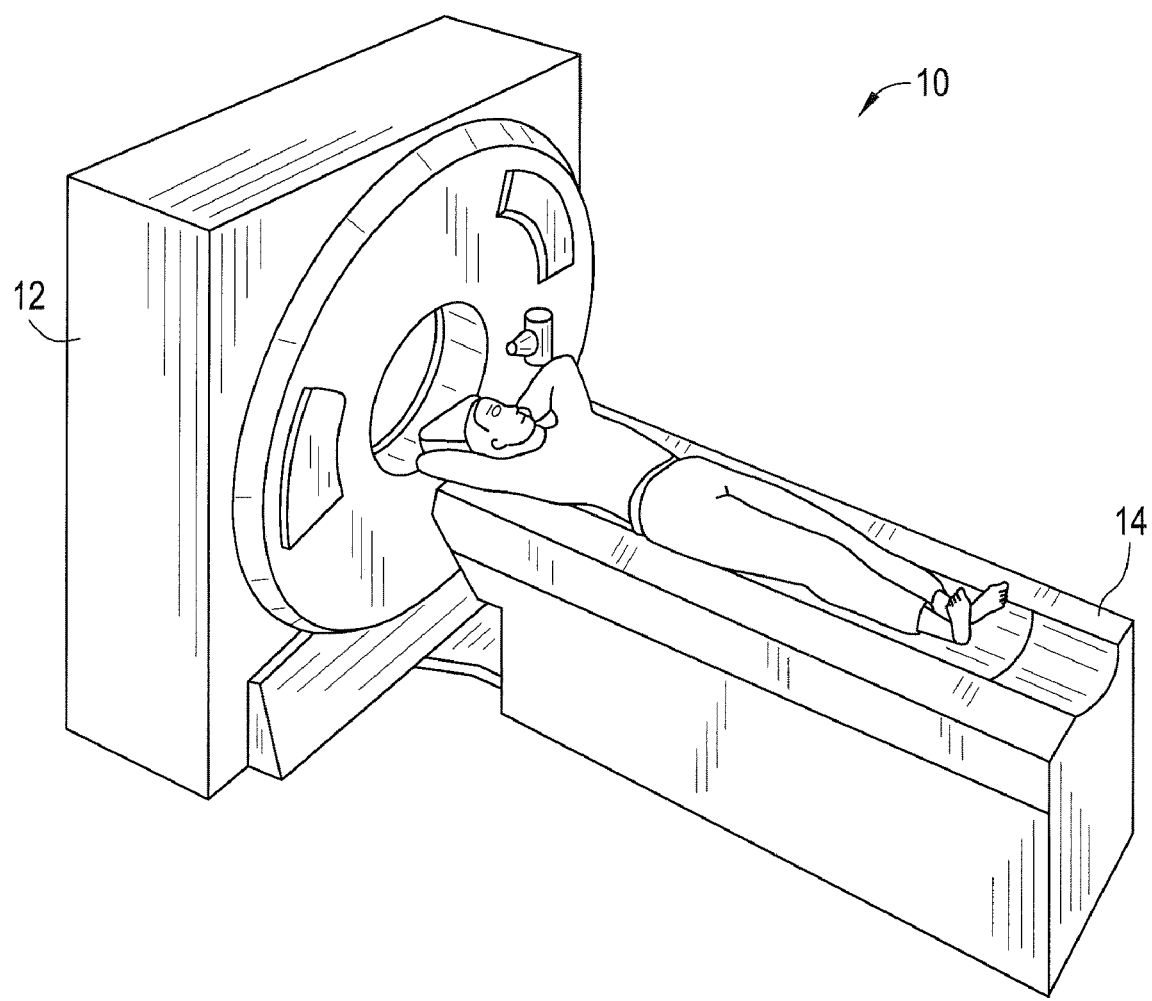
FIG. 1 is a schematic of a CT imaging system in accordance with exemplary embodiment.
Figure 2:
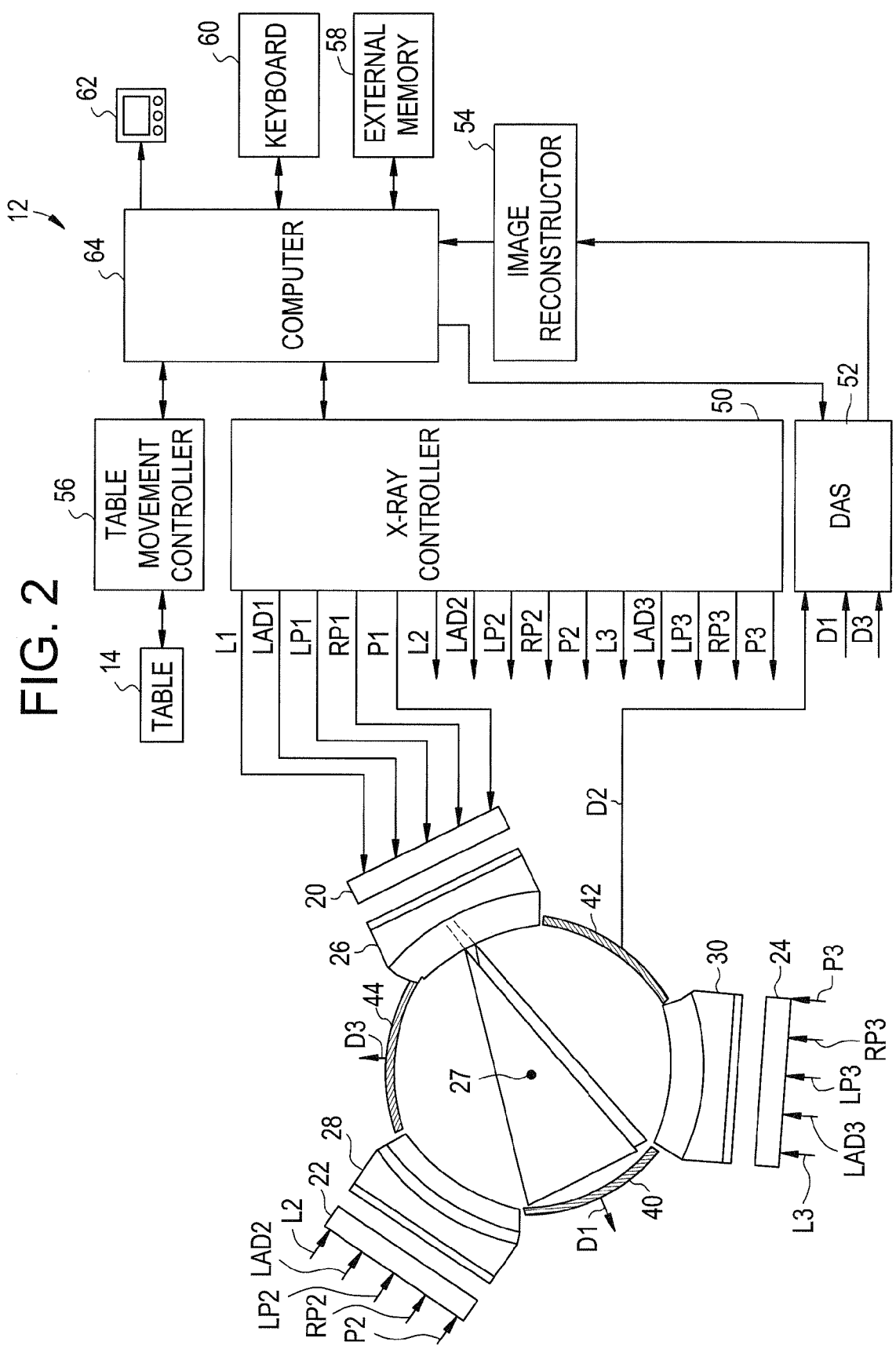
FIG. 2 is a more detailed schematic of the CT imaging system of FIG. 1.

Referring to FIGS. 1 and 2, a CT imaging system 10 for generating digital images of a target object in accordance with an exemplary embodiment is shown. The CT imaging system 10 includes a CT scanning device 12 and a table 14.

The CT scanning device 12 is provided to generate a plurality of digital images of a target object. The CT scanning device 12 includes light emitting assemblies 20, 22, 24, x-ray source assemblies 26, 28, 30, x-ray detector arrays 40, 42, 44, an x-ray controller 50, a data acquisition system 52, an image reconstructor device 54, a table movement controller 56, an external memory 58, a keyboard 60, a display monitor 62, and a computer 64. It should be noted that in an alternate embodiment, CT scanning device 12 can have more than or less than three x-ray source assemblies. Further, CT scanning device 12 can have more than or less than three x-ray detector arrays.

The light emitting assemblies 20, 22, 24 are provided to emit light beams that induce the x-ray source assemblies 26, 28, 30, respectively to emit x-ray beams. X-ray beams from the x-ray source assembly 26 propagate through an object 27 and are received by the x-ray detector array 40. Similarly, x-ray beams from the x-ray source assembly 28 propagate through the object 27 and are received by the x-ray detector array 42. Similarly, x-ray beams from the x-ray source assembly 30 propagate through the object 27 and are received by the x-ray detector array 44. Because the structure of light emitting assembly 20 is substantially similar to the structure of light assemblies 22, 24, only a detailed explanation of light assembly 20 will be provided.

Figure 3:
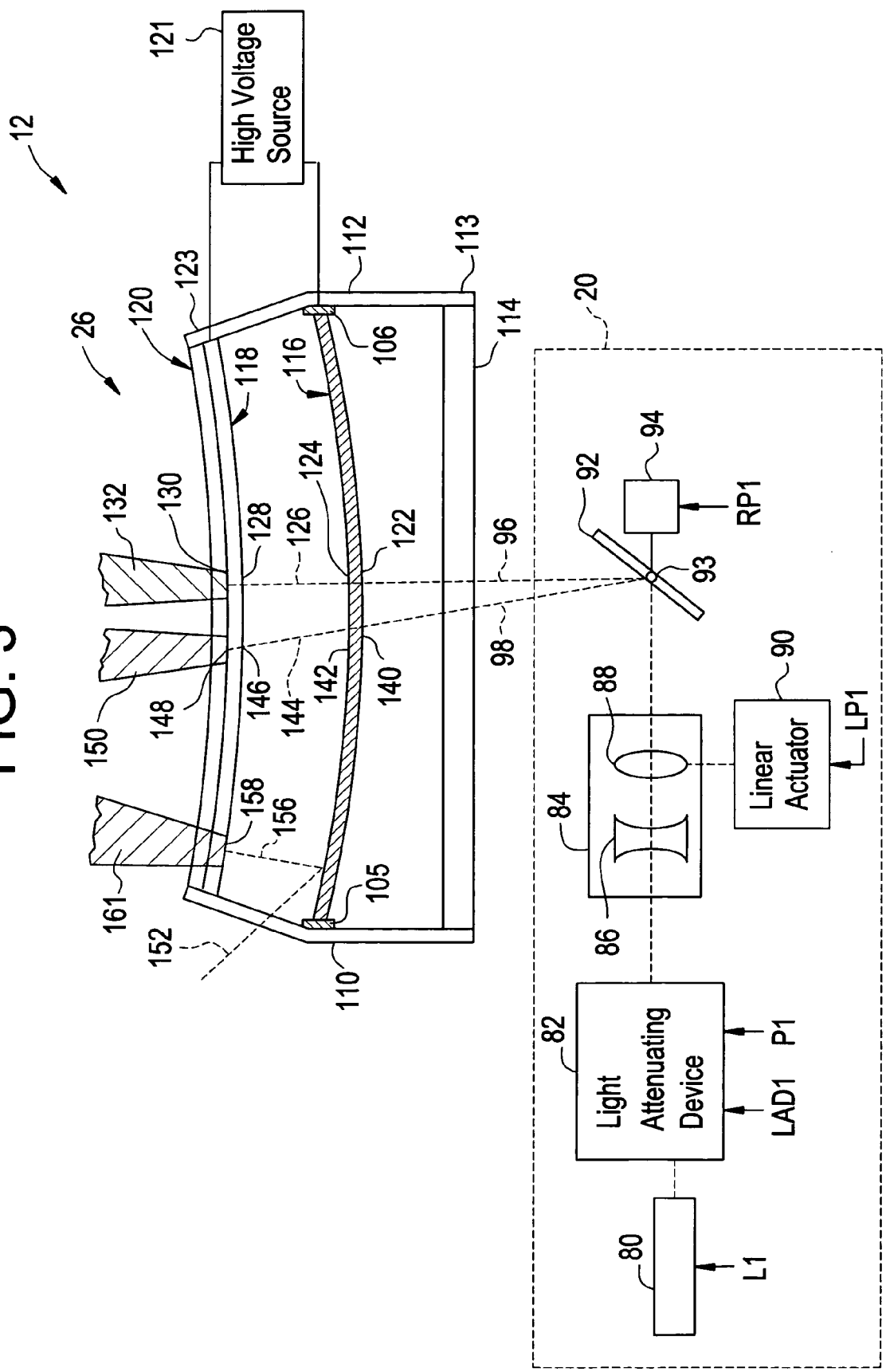
FIG. 3 is a schematic of a light emitting assembly and x-ray source assembly utilized in the CT imaging system of FIG. 1 in accordance with an exemplary embodiment.

Referring to FIG. 3, a more detailed view of the light assembly 20 is illustrated. The light assembly 20 includes a laser 80, a light attenuating device 82, a lens assembly 84, a linear actuator 90, a mirror 92, and a motor 94.

The laser 80 is provided to generate light beams for inducing an x-ray source assembly to emit x-ray beams. The laser 80 comprises a Nd:YAG laser and is disposed proximate the light attenuating device 82. The laser 80 emits a light beam in response to a control signal L1 received from the x-ray controller 50.

Figure 4:
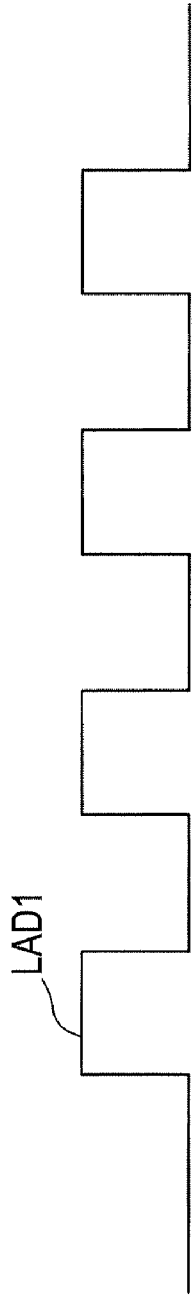
FIG. 4 is a signal schematic of a first digital input signal to a light extenuating device utilized in the light emitting assembly of FIG. 3.
Figure 5:
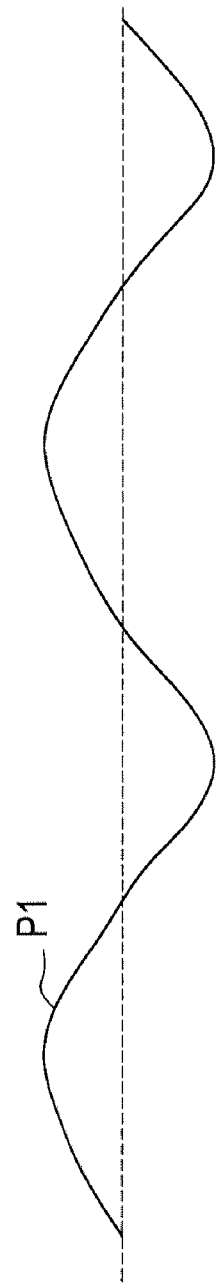
FIG. 5 is a signal schematic of a second analog input signal to the light attenuating device utilized in the light emitting assembly of FIG. 3.
Figure 6:
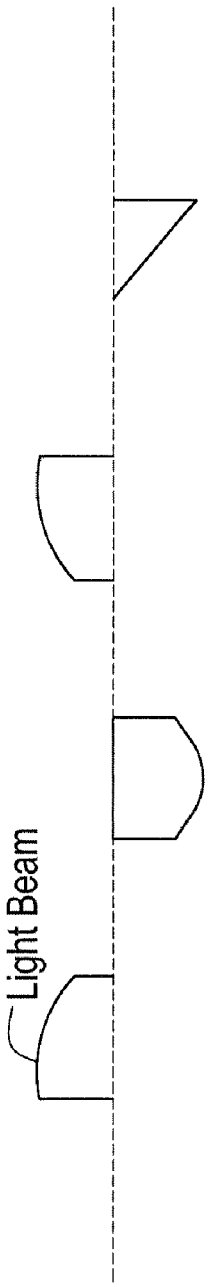
FIG. 6 is a signal schematic of a light output signal from the light attenuating device utilized in the light emitting assembly of FIG. 3.

The light-attenuating device 82 is provided to attenuate an intensity of a light beam received from the laser 80. It should be noted, that by varying an intensity of the light beam, a power level of a subsequently generated electron beam and a power level of an x-ray beam can be varied. The light-attenuating device 82 is disposed between the laser 80 and the lens assembly 84. During operation, the light attenuating device 82 receives a light beam from the laser 80 and attenuates or adjusts an intensity of the light beam before the light beam propagates to the lens assembly 84. The light-attenuating device 82 comprises an acousto-optic modulator that can adjust the attenuation of the light beam based upon one or more input signals. Of course, in alternate embodiments, the light-attenuating device 82 can comprise any device capable of attenuating a light beam from a laser. In particular, referring to FIG. 4, the light-attenuating device 82 can adjust an amount of attenuation of the light beam based upon the frequency of a digital signal LAD1 received from the x-ray controller 50. Alternately, referring to FIG. 5, the light-attenuating device 82 can adjust an amount of attenuation of the light beam based upon a magnitude of an analog signal P1 from the x-ray controller 50. Referring to FIG. 6, during operation, when the signal LAD1 has a high logic level or the analog signal P1 has a magnitude greater than a predetermined value, the light-attenuating device 82 allows the received light beam to pass therethrough. Alternately, when the signal LAD1 has a low logic level or the analog signal P1 has a magnitude less than or predetermined value, the light-attenuating device 82 does not allow the received light beam to pass therethrough. Thus, the light-attenuating device 82 attenuates the intensity of the light beam by intermittently allowing a portion of the light beam to pass therethrough at predetermined time intervals.

Referring to FIG. 3, the lens assembly 84 is provided to adjust a size of the light beam propagating through the lens assembly 84. It should be noted, that by varying a size of the light beam, a size of a subsequently generated electron beam and a size of an x-ray beam can be varied. The lens assembly 84 includes a diverging lens 86 and a converging lens 88. A linear actuator 90 is operably coupled to the converging lens 88 for moving the lens 88 along an axis of the light beam either toward the diverging lens 86 or away from the lens 86. When the lens 88 is moved toward the diverging lens 86, a size of the light beam exiting the lens 88 is decreased. Alternately, when the lens 88 is moved away from the diverging lens 86, a size of the light beam exiting the lens 88 is increased. The linear actuator 90 operably communicates with the x-ray controller 50 and moves the lens 88 in response to a control signal LP1 received from the x-ray controller 50. It should be understood, that alternate lens assemblies can be utilized in the light emitting assembly 20 instead of the lens assembly 84. For example, in an alternate embodiment, the lens assembly can comprise one or more converging lenses operably coupled to a linear actuator.

The mirror 92 is provided to reflect light beams from the laser 80 through a window 114 of the x-ray source assembly 26 onto a photo-cathode 116 disposed within the assembly 26. In response to receiving a light beam 96 in a region 122 of the photo-cathode 116, the photo-cathode 116 emits an electron beam that is received by the anode 118. In response to receiving the emitted electron beam, the anode 118 generates an x-ray beam that propagates through the window 120. The mirror 92 is rotated about a pivot point 93 by the motor 94 in response to a control signal RP1 received from the x-ray controller 50. In particular, the mirror 92 can be rotated about the pivot point 93 at least 120° such that light from the laser 80 can be directed towards predetermined regions of the photo-cathode 116 responsive to the signal RP1.

The x-ray source assemblies 26, 28, 30 are provided to emit x-ray beams that propagate through a target object and toward the x-ray detector arrays 40, 42, 44, respectively. Because the structure of the x-ray source assembly 26 is substantially similar to the structure of x-ray source assemblies 28 and 30, only a detailed explanation of x-ray source assembly 26 will be provided.

The x-ray source assembly 26 includes outer walls 110, 112, a window 114, a photo-cathode 116, insulating supports 105, 106, an anode 118, a window 120, and a high voltage source 121. The x-ray source assembly 26 further includes front and rear walls (not shown) coupled to walls 110, 112 to form a vacuum chamber therebetween. The window 114 is configured to receive light beams from light emitting assembly 20 and is disposed between the outer walls 110 and 112 at an end 113 of the assembly 26. The insulating supports 105, 106 are coupled to the outer walls 110, 112 respectively. The insulating supports 105, 106 electrically isolate the photo-cathode 116 from the outer walls 110, 112 and holds the photo-cathode 116 therebetween. The photo-cathode 116 comprises a metallic layer configured to emit an electron beam in response to receiving a light beam. In particular, the photo-cathode 116 can be constructed from one or more of the following materials: gold (Au), silver (Ag), copper (Cu), magnesium (Mg), yttrium (Y), calcium (Ca), indium gallium arsenide (InGaAs), gallium arsenide (GeAs), gallium arsenide phosphide (GaAsP), gallium aluminum arsenide (GaAlAs), cadium telluride ($CdTe_2$), cesium telluride ($Cs_2Te$), or sodium potassium antimonide ($Na_2KSb$). Alternately, the photo-cathode 116 can be constructed from an alloy containing gold, silver, or copper. Further, the photo-cathode 116 can have a thickness of 50–500 microns. Of course, the photo-cathode 116 can have a thickness less than 50 microns or greater than 500 microns based upon desired operational characteristics. The anode 118 is disposed between walls 110, 112 at an end 123 of the assembly 26. The window 120 is disposed proximate the anode 118 between walls 110, 112 and allows x-ray beams emitted from the anode 118 to pass therethrough out of the assembly 26. The high voltage source 121 is electrically coupled between the anode 118 and the photo-cathode 116 and accelerates electron beams emitted from the photo-cathode 116 toward the anode 118. In an alternate embodiment, the walls 110, 112 can be constructed of a substantially transparent material, such as a glass, to allow light beams to pass therethrough to contact a side of the photo-cathode 116 that is facing to the anode 118.

Referring again to FIG. 2, the data acquisition system 52 is operably coupled to the x-ray detector arrays 40, 42, 44, the computer 64, and to the image reconstructor 54. The data acquisition system 52 samples signals D1, D2, D3 from the x-ray detector arrays 40, 42, 44, respectively and transfers sampled values indicative of the signals to the image reconstructor 54.

The image reconstructor 54 is provided to generate digital images based on the signals D1, D2, D3. The image reconstructor 54 is operably coupled between the data acquisition system 52 and the computer 64. The image reconstructor 54 transmits the generated digital images to the computer 64.

Referring to FIG. 2, the x-ray controller 50 is provided to control the CT scanner 12 in response to a control signal received from the computer 64. The x-ray controller 50 is operably coupled to the light emitting assemblies 20, 22, 24 and the computer 64. The x-ray controller 50 generates control signals L1, LAD1, LP1, RP1, that are received by the light emitting assembly 20 to control operation of the laser 80, a power level of a light beam exiting light-attenuating device 82, a size of a light beam exiting lens assembly 84, and an operational position of the mirror 92, respectively. Alternately, the x-ray controller 50 can generate an analog control signal P1 instead of signal LAD1 to control a power level of the light beam exiting light attenuating device 82. X-ray controller 50 generates control signals L2, LAD2, P2, LP2, RP2 that are received by the light emitting assembly 22 for operational purposes substantially similar to signals L1, LAD1, P1, LP1, RP1, respectively. Further, x-ray controller 50 generates control signals L3, LAD3, P3, LP3, RP3 that are received by the light emitting assembly 24 for operational purposes substantially similar to signals L1, LAD1, P1, LP1, RP1, respectively.

The computer 64 is operably coupled to the x-ray controller 50, the data acquisition system 52, the image reconstructor 54, the external memory 58, a keyboard 60, a computer monitor 62, and the table movement controller 56. The computer 64 is provided to generate a first control signal that induces the table movement controller 56 to move the table 14. Further, the computer 64 generates a second control signal that induces the x-ray controller 50 to initiate generating x-ray beams. Further, the computer 56 receives the generated digital images from the image reconstructor 54 and either displays the images on the display monitor 62 or stores the digital images in the external memory 58, or both. The keyboard 60 is operably coupled to the computer 64 to allow user to request specific digital images to view.

Figure 7:
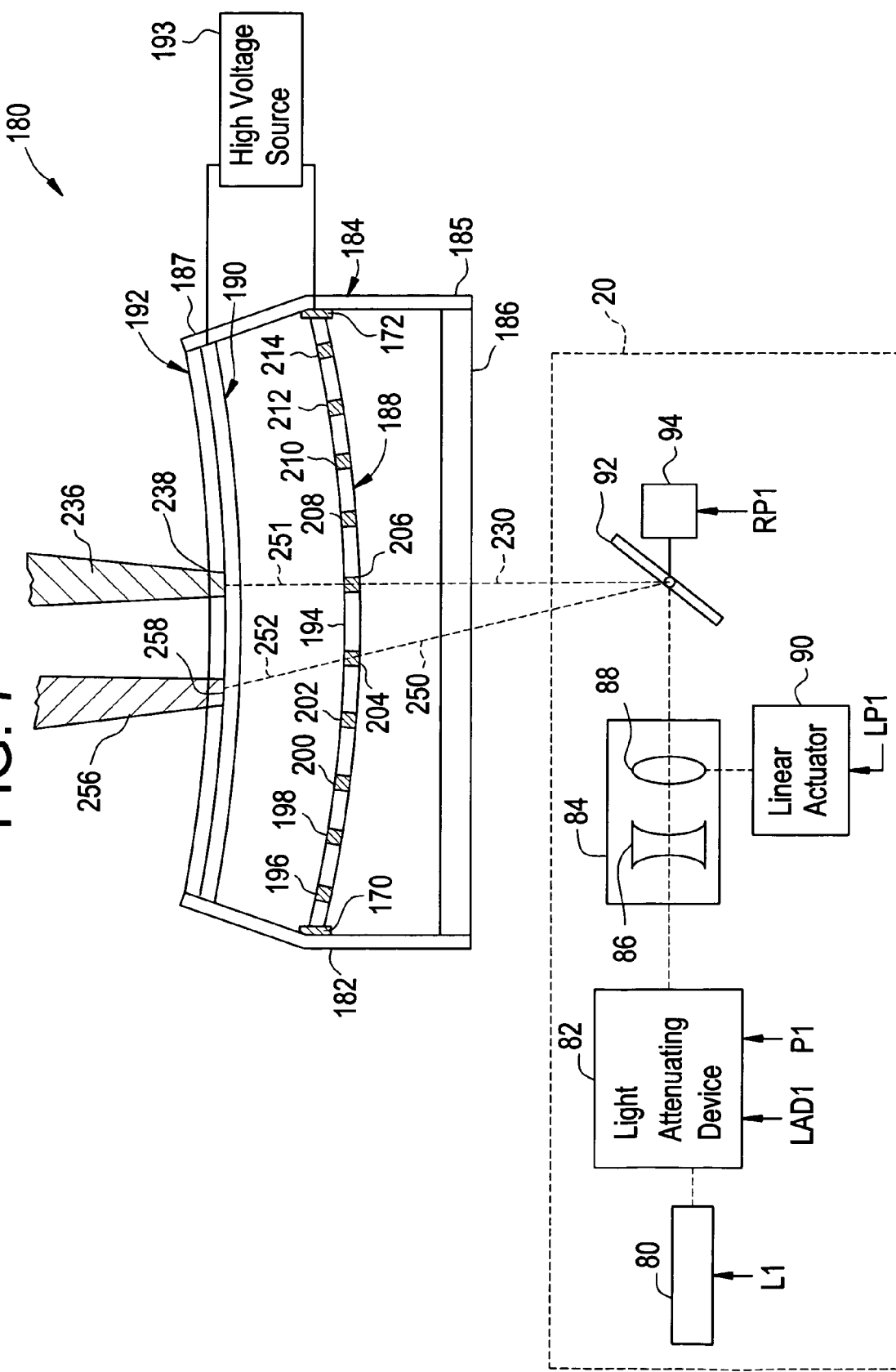
FIG. 7 is a schematic of a light emitting assembly and x-ray source assembly that can be utilized in the CT imaging system of FIG. 1 in accordance with another exemplary embodiment.

Referring to FIG. 7, an alternate embodiment of a CT scanning device 12 will be explained. In this embodiment, each of the x-ray source assemblies 26, 28, 30, shown in FIG. 1, are replaced with an x-ray source assembly 180. The x-ray source assembly 180 receives one or more light beams from the light emitting assembly 20 and then emits one or more x-ray beams responsive to the light beams.

Figure 8:
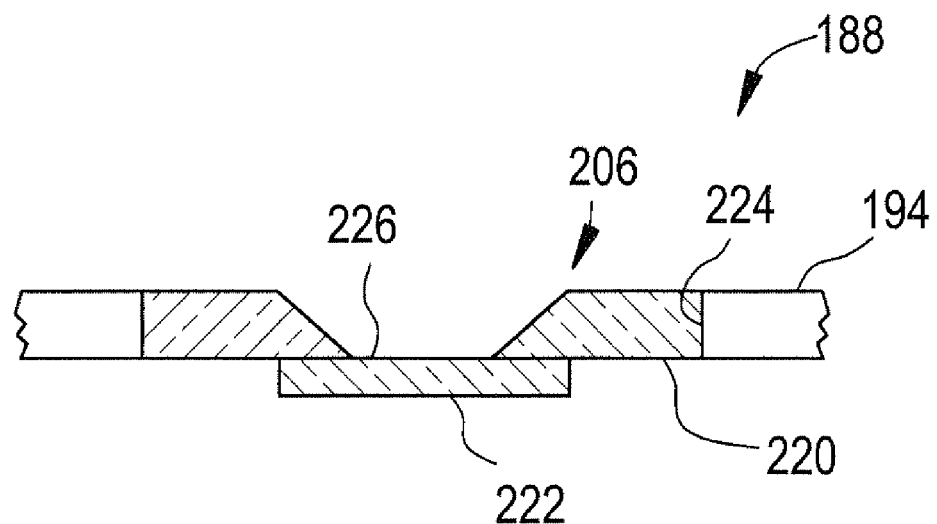
FIG. 8 is a cross-sectional of view of the portion of the photo-cathode utilized in the x-ray source assembly of FIG. 7.
Figure 9:
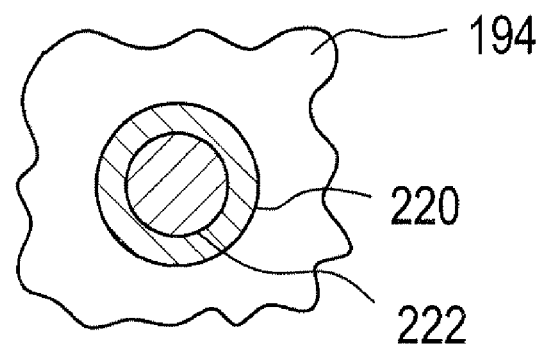
FIG. 9 is a top view of the portion of the photo-cathode utilized in the x-ray source assembly of FIG. 7.

Referring to FIGS. 7–9, a cross-sectional view of the x-ray source assembly 180 is shown. The x-ray source assembly 180 includes outer walls 182, 184, a window 186, a photo-cathode 188, insulating supports 170, 172, an anode 190, a window 192, and a high voltage source 193. The x-ray source assembly 180 further includes front and rear walls (not shown) coupled to walls 182, 184 to form a vacuum chamber therebetween. The window 186 is disposed between the outer walls 182, 184 at an end 185 of the assembly 180. The insulating supports 170, 172 are coupled to the outer walls 182, 184, respectively. The insulating supports 170, 172 electrically isolate the photo-cathode 188 from the outer walls 182, 184, respectively. The photo-cathode 188 comprises a substrate 194 and includes a two dimensional array of metallic regions extending through the substrate 194, wherein one row of the metallic regions includes metallic regions 196, 198, 200, 202, 204, 206, 208, 210, 212, 214. The substrate 194 can be constructed from a non-metallic material, such as a glass for example. In an alternate embodiment, the substrate 194 can be constructed from a metallic material, such as stainless steel for example. The metallic regions to be constructed from one or more of the following materials: gold (Au), silver (Ag), copper (Cu), magnesium (Mg), yttrium (Y), calcium (Ca), indium gallium arsenide (InGaAs), gallium arsenide (GeAs), gallium arsenide phosphide (GaAsP), gallium aluminum arsenide (GaAlAs), cadium telluride ($CdTe_2$), cesium telluride ($Cs_2Te$), or sodium potassium antimonide ($Na_2KSb$). Alternately, the metallic regions can be constructed from an alloy containing gold, silver, or copper. Further, the metallic regions can have a thickness of 50–500 microns. Of course, the metallic regions can have a thickness less than 50 microns or greater than 500 microns based upon desired operational characteristics. Because the structure of the metallic regions are substantially similar to one another, only a detailed explanation of the structure of the metallic region 206 will be provided. The metallic region 206 includes a metallic member 220 and a metallic member 222. The metallic member 220 is disposed within an aperture 224 that extends through the substrate 194. The metallic member 220 includes a conically-shaped aperture 226 extending therethrough. The metallic member 222 has a circular cross-sectional shape and is disposed over a portion of the aperture 226. The member 222 can have an area in a range of 1–2 square centimeters. The conically-shaped aperture 226 induces the metallic member 222 to emit an electron beam that is substantially cylindrically-shaped in response to receiving a light beam. The conically-shaped aperture 206 focuses the electron beam to keep the electron beam from diverging. The anode 190 is disposed between walls 182, 184 at an end 187 of the assembly 180. The window 192 is disposed between the walls 182, 184 proximate the anode 190 and allows x-ray beams emitted from the anode 190 to pass therethrough out of the assembly 180. The high voltage source 193 is electrically coupled between the anode 190 and the photo-cathode 188 and accelerates electron beams emitted from the photo-cathode 188 towards the anode 190.

In an alternate embodiment, the walls 182, 184 of the x-ray source assembly 180 can be constructed of a substantially transparent material, such as a glass, to allow a light beam to pass therethrough that contacts a side of the photo-cathode 188 proximate to the anode 190.

During operation of the x-ray source assembly 180, when the metallic region 206 receives a light beam 230, the metallic region 206 emits an electron beam 251 toward the anode 190 in response to the light beam 230. Thereafter, the anode 190 emits an x-ray beam 236 from a region 238 on the anode 190 in response to receiving the electron beam 251. Similarly, when the metallic region 204 receives a light beam 250, the metallic region 204 emits an electron beam 252 toward the anode 190 in response to the light beam 250. Thereafter, the anode 190 emits an x-ray beam 256 from a region 258 on the anode 190 in response to receiving the electron beam 252.

Figure 10:
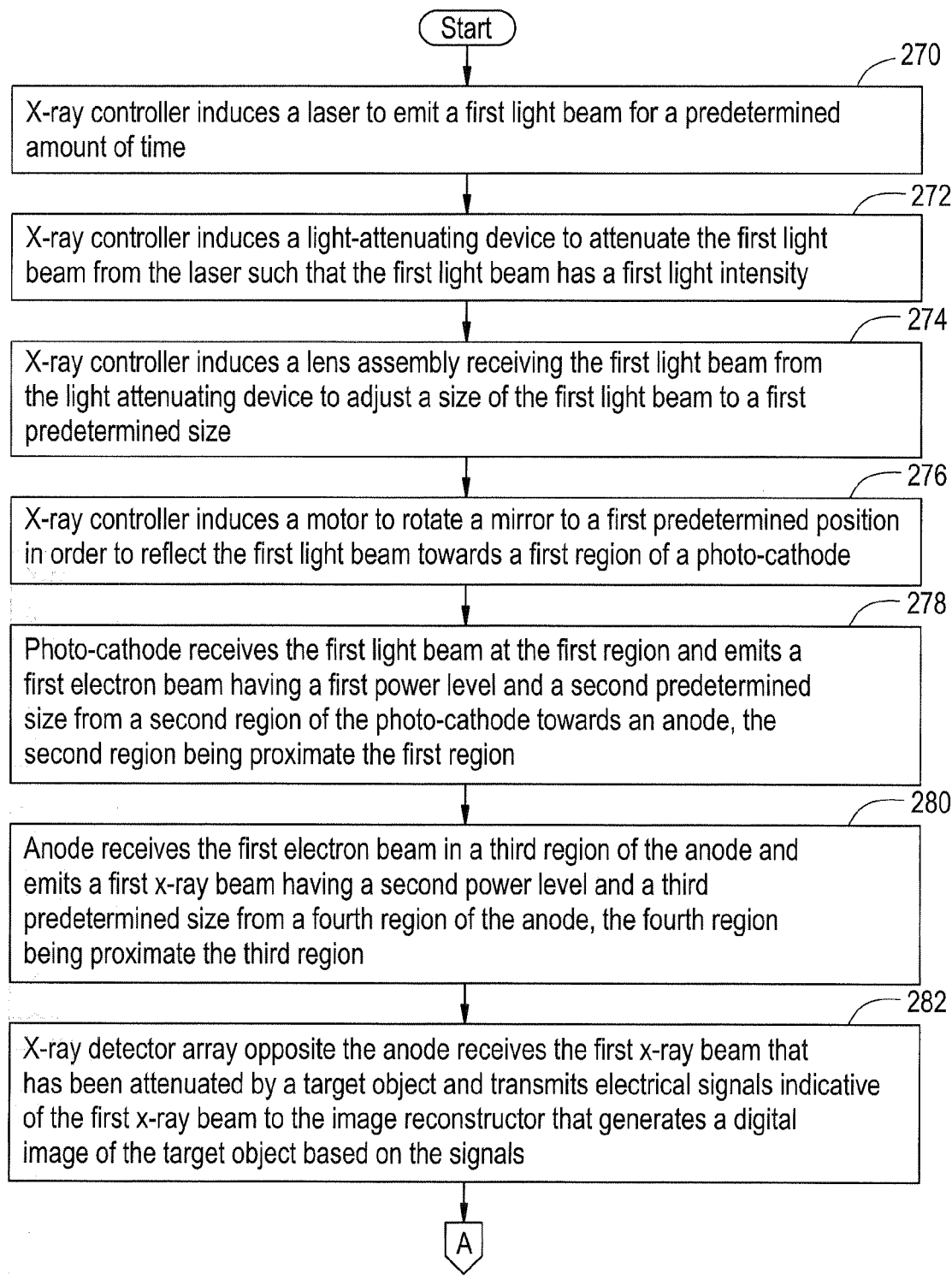
FIGS. 10–12 are flowcharts of a method for generating x-ray beams and varying the power, size, and position of x-ray beams utilizing the CT imaging system of FIG. 1 in accordance with an exemplary embodiment.
Figure 11:
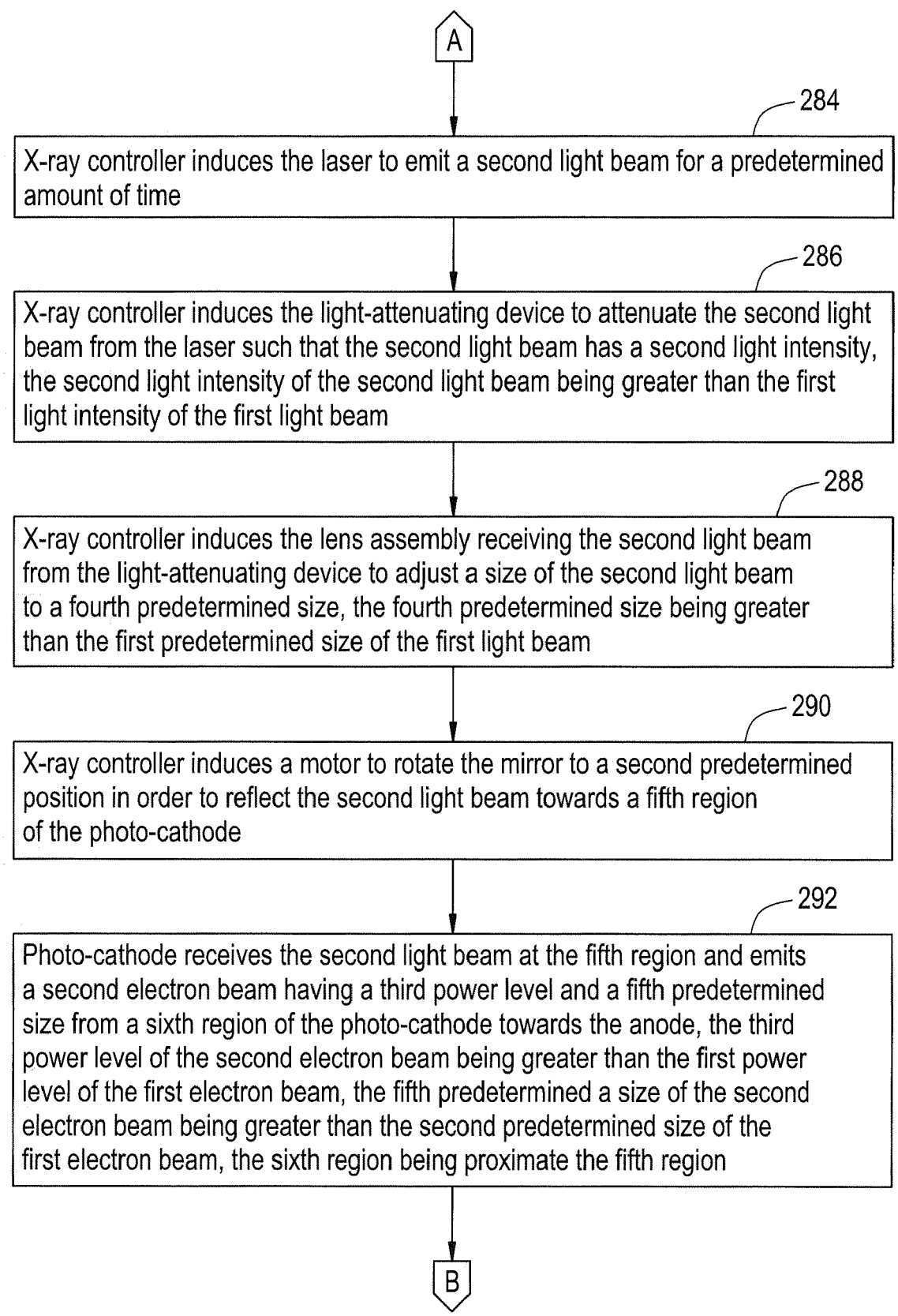
Figure 12:
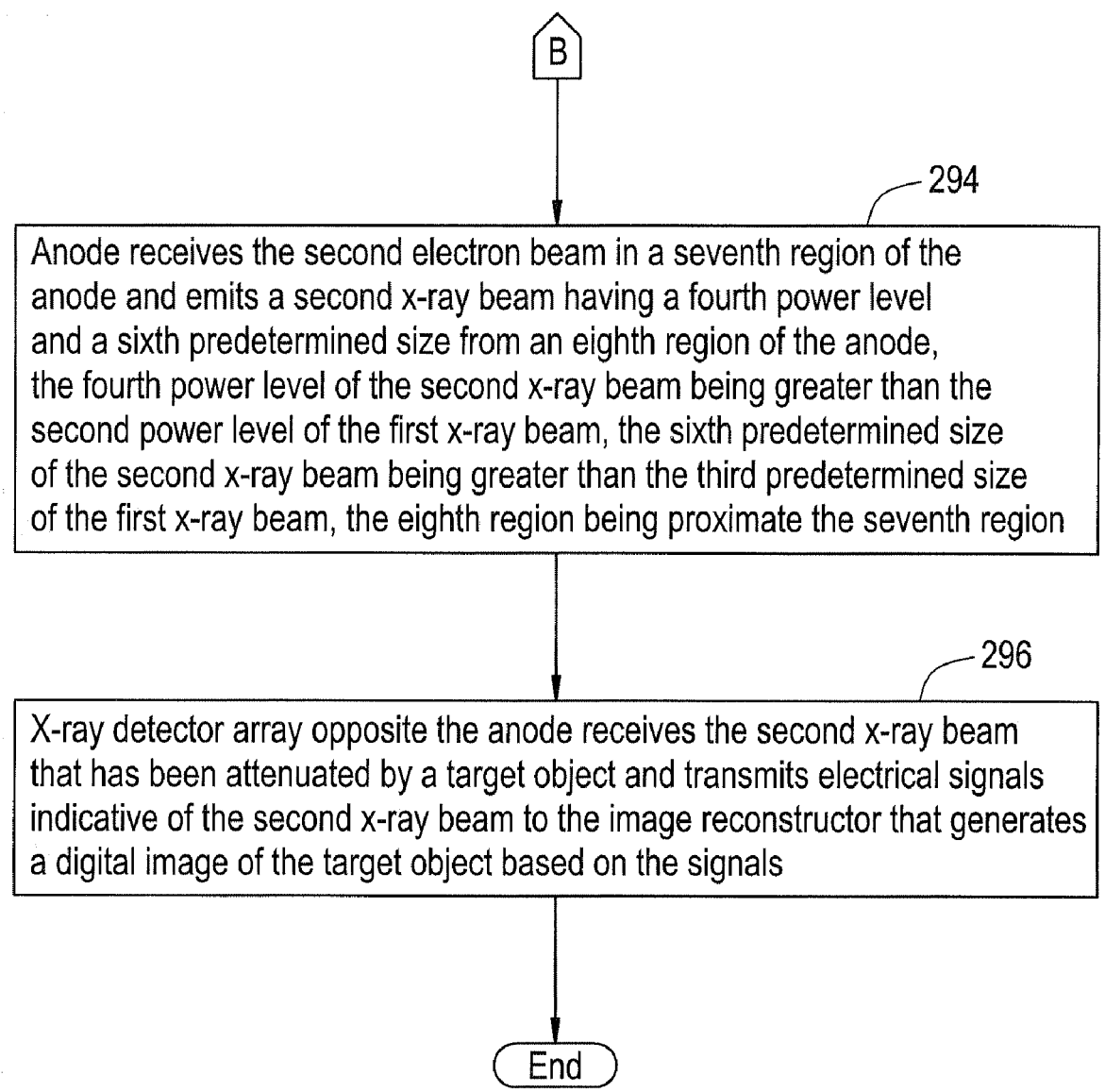

Referring to FIGS. 10–12, a method varying a power and a position of electron beams and x-ray beams will now be explained. In particular, the method will be explained utilizing the CT scanning device 12 with the light source assembly 20, the x-ray source assembly 26, and the x-ray detector array 40. It should be understood that the method is also performed for the other light source assemblies, x-ray source assemblies, and the x-ray detector arrays. Further, the method could also be implemented utilizing the light source assembly 20 with the x-ray source assembly 180, instead of the x-ray source assembly 26.

At step 270, the x-ray controller 50 induces the laser 80 to emit a light beam 96 for a predetermined amount of time.

At step 272, the x-ray controller 50 induces the light-attenuating device 82 to attenuate the light beam 96 from the laser 80 such that the light beam 96 has a first light intensity.

At step 274, the x-ray controller 50 induces a lens assembly 84 receiving the light beam 96 from the light-attenuating device 82 to adjust a size of the light beam 96 to a first predetermined size.

At step 276, the x-ray controller 50 induces the motor 94 to rotate the mirror 92 to a first predetermined position in order to reflect the light beam 96 towards region 122 of the photo-cathode 116.

At step 278, the photo-cathode 116 receives the light beam 96 at the region 122 and emits an electron beam 126 having a first power level and a second predetermined size from a region 124 of the photo-cathode 116 towards the anode 118, the region 124 being proximate the region 122.

At step 280, the anode 118 receives the electron beam 126 in a region 128 of the anode 118 and emits an x-ray beam 132 having a second power level and a third predetermined size from a region 130 of the anode 118, the region 130 being proximate the region 128.

At step 282, the x-ray detector array 40 opposite the anode 118 receives the x-ray beam 132 that has been attenuated by the target object 27 and transmits electrical signals indicative of the x-ray beam 132 to the image reconstructor 54 that generates a digital image of the target object 27 based on the signals.

At step 284, the x-ray controller 50 induces the laser 80 to emit a light beam 98 for a predetermined amount of time.

At step 286, the x-ray controller 50 induces the light-attenuating device 82 to attenuate the light beam 98 from the laser 80 such that the light beam 98 has a second light intensity, the second light intensity of the light beam 98 being greater than the first light intensity of the light beam 96.

At step 288, the x-ray controller 50 induces the lens assembly 84 receiving the light beam 98 from the light-attenuating device 82 to adjust a size of the light beam 98 to a fourth predetermined size, the fourth predetermined size being greater than the first predetermined size of the light beam 96.

At step 290, the x-ray controller 50 induces the motor 94 to rotate the mirror 92 to a second predetermined position in order to reflect the light beam 98 towards a region 140 of the photo-cathode 116.

At step 292, the photo-cathode 116 receives the light beam 98 at the region 140 and emits an electron beam 144 having a third power level and a fifth predetermined size from a region 142 of the photo-cathode 116 towards the anode 118, the third power level of the electron beam 144 being greater than the first power level of the electron beam 126, the fifth predetermined size of the electron beam 144 being greater than the second predetermined size of the electron beam 126, the region 142 being proximate the region 140.

At step 294, the anode 118 receives the electron beam 144 in a region 146 of the anode 118 and emits an x-ray beam 150 having a fourth power level and a sixth predetermined size from a region 148 of the anode 118, the fourth power level of the x-ray beam 150 being greater than the second power level of the x-ray beam 132, the sixth predetermined size of the x-ray beam 150 being greater than the third predetermined size of the x-ray beam 132, the region 148 being proximate the region 146.

At step 296, the x-ray detector array 40 opposite the anode 118 receives the x-ray beam 150 that has been attenuated by the target object 27 and transmits electrical signals indicative of the x-ray beam 150 to the image reconstructor 54 that generates a digital image of the target object 27 based on the signals.

It should be noted that in an alternate embodiment of x-ray source assembly 26, the light emitting assembly 20 emits a light beam through a window (not shown) in the outer wall 110 onto the photo-cathode 116 instead of emitting light through the window 114. In particular, the light emitting assembly 20 emits a light beam 152 onto the photo-cathode 116. Thereafter, the photo-cathode 116 emits an electron beam 156 towards a region 158 on the anode 118. In response to receiving the electron beam 156, the anode 118 emits an x-ray beam 161 toward the x-ray detector array 40.

Figure 13:
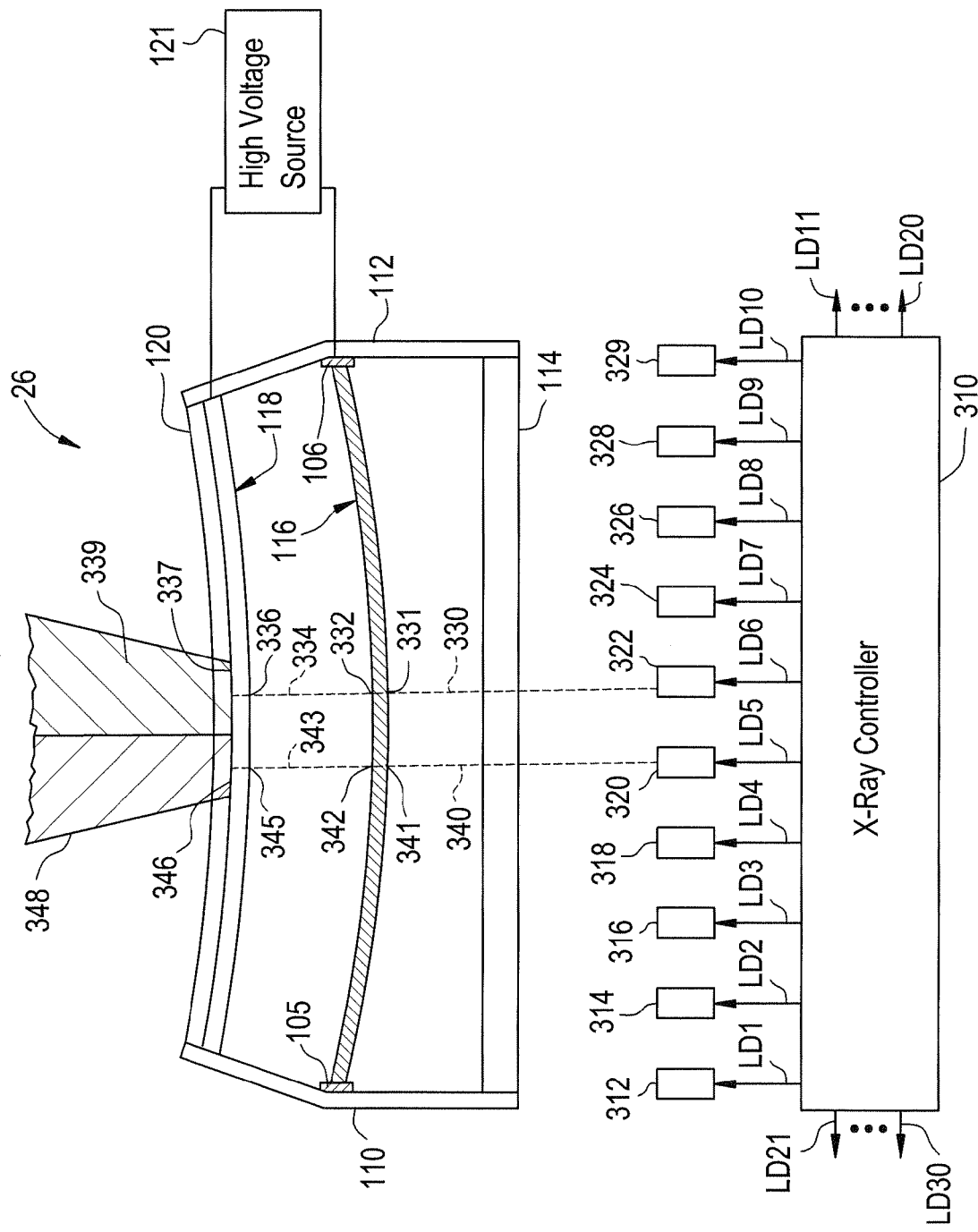
FIG. 13 is a schematic of a light emitting assembly and x-ray source assembly that can be utilized in the CT imaging system of FIG. 1 in accordance with another exemplary embodiment.

Referring to FIG. 13, an alternate embodiment of the CT scanning device 12 will be explained. In this embodiment, the x-ray controller 50 can be replaced with x-ray controller 310 and the light emitting assembly 20 can be replaced with the laser diodes 312, 314, 316, 318, 320, 322, 324, 326, 328, 329. Similarly, the light emitting assemblies 22, 24 could be replaced with laser diodes disposed proximate the x-ray source assemblies 28, 30.

The x-ray controller 310 is electrical coupled to the laser diodes and generates control signals LD1, LD2, LD3, LD4, LD5, LD6, LD7, LD8, LD9, LD10 to control when laser diodes 312, 314, 316, 318, 320, 322, 324, 326, 328, 329, respectively, emit light beams toward the photo-cathode 116 of the x-ray source assembly 26. The x-ray controller 310 also generates control signals LD11–LD20 for inducing laser diodes (not shown) to emit light beams toward the x-ray source 28 and control signals LD21–30 for inducing laser diodes (not shown) to emit light beams toward the x-ray source assembly 30. The x-ray controller 310 determines which of the laser diodes to turn on and a predetermined time interval for maintaining energization of the laser diodes.

Figure 14:
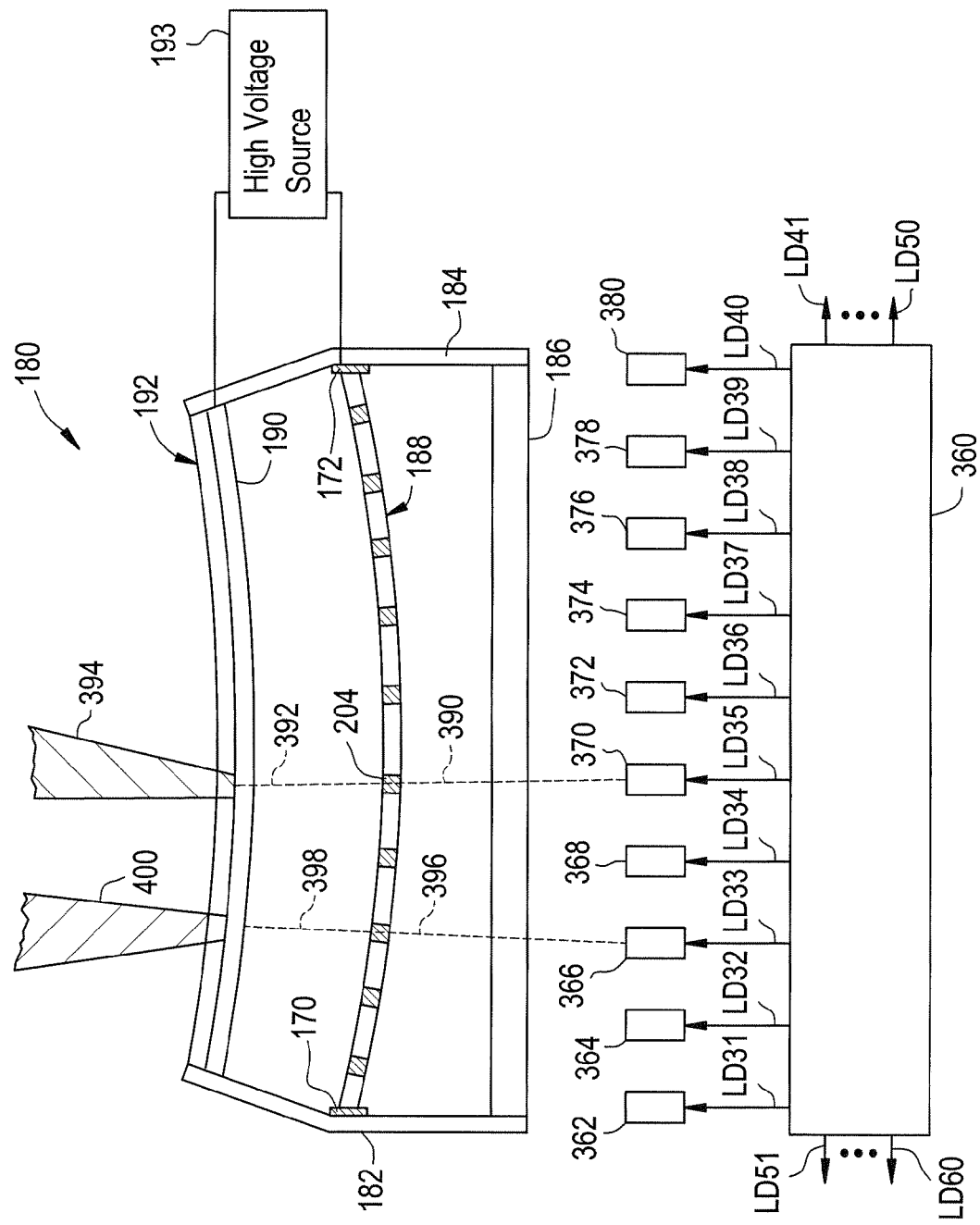
FIG. 14 is a schematic of a light emitting assembly and x-ray source assembly that can be utilized in the CT imaging system of FIG. 1 in accordance with another exemplary embodiment.

Referring to FIG. 14, another alternate embodiment of the CT scanning device 12 will be explained. In this embodiment, the x-ray controller 50 can be replaced with an x-ray controller 360, the light emitting assembly 20 can be replaced with the laser diodes 362, 364, 366, 368, 370, 372, 374, 376, 378, 380, and the x-ray source assembly can be replaced with the x-ray source assembly 180. Further, the light emitting assemblies 22, 24 can be replaced with laser diodes and each of the x-ray source assemblies 28, 30 can be replaced with an x-ray source assembly 180.

The x-ray controller 360 is electrical coupled to the laser diodes and generates control signals LD31, LD32, LD33, LD34, LD35, LD36, LD37, LD38, LD39, LD40 to control when laser diodes 362, 364, 366, 368, 370, 372, 374, 376, 378, 380, respectively, emit light beams toward the photo-cathode 188 of the x-ray source assembly 180. The x-ray controller 360 also generates control signals LD41–LD50 for inducing laser diodes (not shown) to emit light beams toward another x-ray source assembly 28 and control signals LD51–LD60 for inducing laser diodes (not shown) to emit light beams toward still another x-ray source assembly. The x-ray controller 360 determines which of the laser diodes to turn on and a predetermined time interval for maintaining energization of the laser diodes. Each of the laser diodes 362–380 are disposed proximate a corresponding metallic region of the photo-cathode 188 to emit a light beam toward the metallic region.

During operation, for example, x-ray controller 360 induces the laser diode 370 to generate a light beam 390 toward the metallic region 204 of the photo-cathode 188. In response, the photo-cathode 188 emits an electron beam 392 toward the anode 190 that induces the anode 190 to emit an x-ray beam 394. Similarly, the x-ray controller 360 induces laser diode 366 to generate a light beam 396 toward a metallic region of the photo-cathode 188. In response, the photo-cathode 188 emits an electron beam 398 toward the anode 190 that induces the anode 190 to emit an x-ray beam 400.

Figure 15:
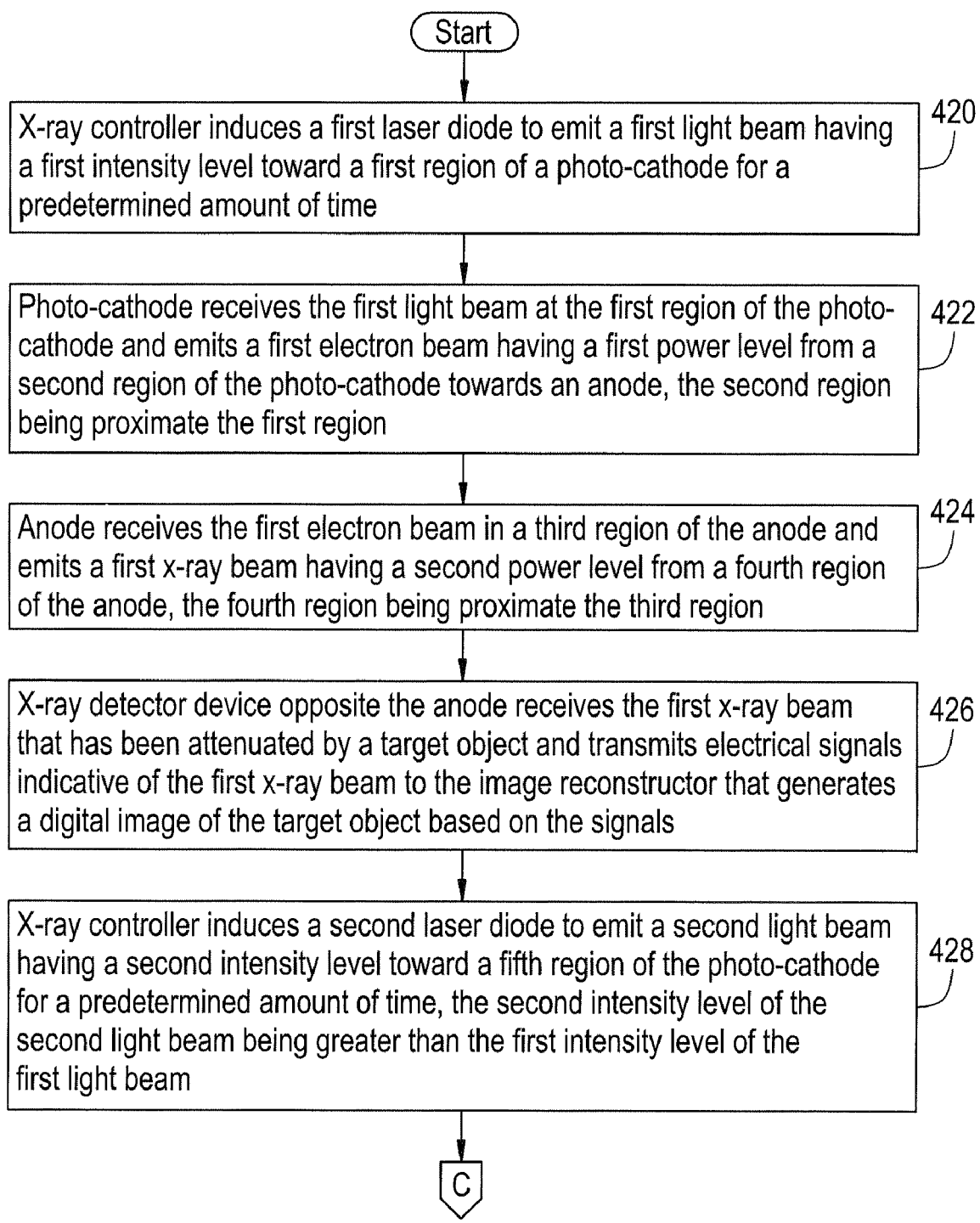
FIGS. 15–16 are flowcharts of a method for generating x-ray beams and varying a power and a position of the x-ray beams utilizing the light emitting assembly and x-ray source assembly of FIG. 13 in accordance with another exemplary embodiment.
Figure 16:
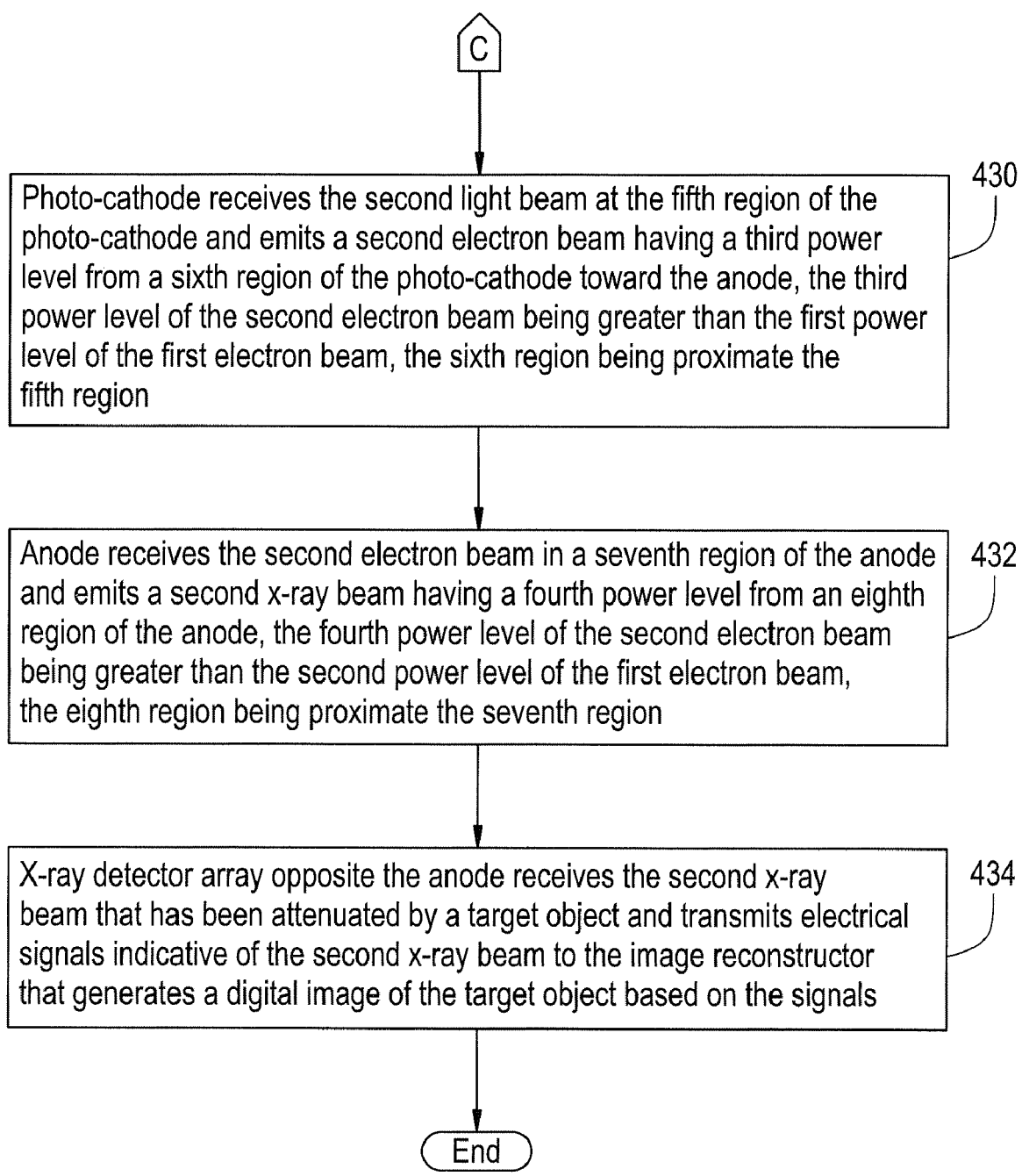

Referring to FIGS. 15–16, a method for varying a power and a position of electron beams and x-ray beams utilizing the CT scanning device shown in FIG. 13 will now be explained. It should be noted that the method could also be implemented utilizing the CT scanning device shown in FIG. 14.

At step 420, the x-ray controller 310 induces a laser diode 322 to emit a light beam 330 having a first intensity level toward a region 331 of the photo-cathode 116 for a predetermined amount of time.

At step 422, the photo-cathode 116 receives the light beam 330 at the region 331 of the photo-cathode 116 and emits an electron beam 334 having a first power level from a region 332 of the photo-cathode 116 towards an anode 118, the region 332 being proximate the region 331.

At step 424, the anode 118 receives the electron beam 334 in a region 336 of the anode 118 and emits an x-ray beam 339 having a second power level from a region 337 of the anode 118, the region 337 being proximate the region 336.

At step 426, the x-ray detector device 40 opposite the anode 118 receives the x-ray beam 339 that has been attenuated by the target object 27 and transmits electrical signals indicative of the x-ray beam 339 to the image reconstructor 54 that generates a digital image of the target object 27 based on the signals.

At step 428, the x-ray controller 310 induces the laser diode 320 to emit a light beam 340 having a second intensity level toward a region 341 of the photo-cathode 116 for a predetermined amount of time, the second intensity level of the light beam 340 being greater than the first intensity level of the light beam 330.

At step 430, the photo-cathode 116 receives the light beam 340 at the region 341 of the photo-cathode 116 and emits an electron beam 343 having a third power level from a region 342 of the photo-cathode 116 toward the anode 118, the third power level of the electron beam 343 being greater than the first power level of the electron beam 334, the region 342 being proximate the region 341.

At step 432, the anode 118 receives the electron beam 343 in a region 345 of the anode 118 and emits an x-ray beam 348 having a fourth power level from an region 346 of the anode 118, the fourth power level of the electron beam 343 being greater than the second power level of the electron beam 334, the region 346 being proximate the region 345.

At step 434, the x-ray detector array 40 opposite the anode 118 receives the x-ray beam 348 that has been attenuated by the target object 27 and transmits electrical signals indicative of the x-ray beam 348 to the image reconstructor 54 that generates a digital image of the target object 27 based on the signals.

Figure 17:
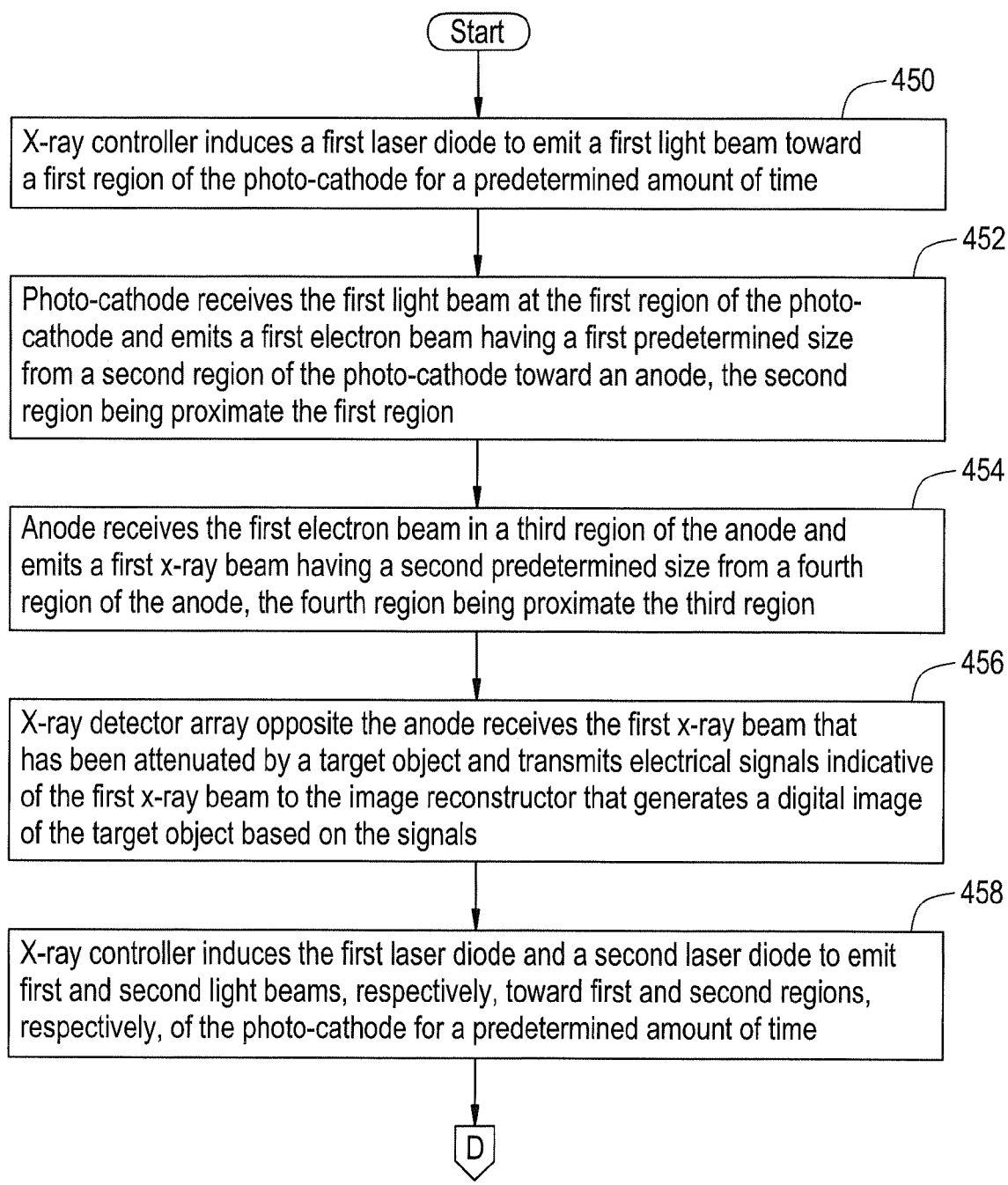

Referring to FIGS. 17–18, a method for varying a size of the x-ray beams utilizing the CT scanning device shown in FIG. 13 will now be explained. It should be noted that the method could also be implemented utilizing the CT scanning device shown in FIG. 14.

At step 450, the x-ray controller 310 induces the laser diode 322 to emit a light beam 330 toward a region 331 of the photo-cathode 116 for a predetermined amount of time.

At step 452, the photo-cathode 116 receives the light beam 330 at the region 331 of the photo-cathode 116 and emits an electron beam 334 having a first predetermined size from a region 332 of the photo-cathode 116 toward the anode 118, the region 332 being proximate the region 331.

At step 454, the anode 118 receives the electron beam 334 in a region 336 of the anode 118 and emits an x-ray beam 339 having a second predetermined size from the region 337 of the anode 118, the region 337 being proximate the region 336.

At step 456, the x-ray detector array 40 opposite the anode 118 receives the x-ray beam 339 that has been attenuated by the target object 27 and transmits electrical signals indicative of the x-ray beam 339 to the image reconstructor 54 that generates a digital image of the target object 27 based on the signals.

At step 458, the x-ray controller 50 induces the laser diodes 322, 320 to both emit light beams 330, 340, respectively, toward regions 331, 341, respectively, of the photo-cathode 116 for a predetermined amount of time.

At step 460, the photo-cathode 116 receives the light beams 330, 340 at the regions 331, 341, respectively, of the photo-cathode 116 and emits a second electron beam, comprising both electron beams 334, 343, having a third predetermined size from a region, comprising both regions 332, 342, of the photo-cathode 116 towards the anode 118, the third predetermined size of the electron beams 334, 343 being greater than the first predetermined size of the electron beam 334, the region comprising both regions 332, 342 being proximate the regions 331, 341.

At step 462, the anode 118 receives the second electron beam in a sixth region of the anode 118 and emits a second x-ray beam, comprising both x-ray beams 339, 348, having a fourth predetermined size from a seventh region of the anode 118, the fourth predetermined size of the second x-ray beam being greater than the second predetermined size of the x-ray beam 339, the seventh region being proximate the sixth region.

At step 464, the x-ray detector array 40 opposite the anode 118 receives the second x-ray beam that has been attenuated by the target object 27 and transmits electrical signals indicative of the second x-ray beam to the image reconstructor 54 that generates a digital image of the target object 27 based on the signals.

The system and method for generating an electron beam and x-ray beams provide a substantial advantage over other systems and methods. In particular, the system provides a technical effect of changing a position of an electron beam and thus an x-ray beam without the electron emitter device being rotated about an axis.

While embodiments of the invention are described with reference to the exemplary embodiments, it will be understood by those skilled in the art that various changes may be made and equivalence may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling with the scope of the intended claims. Moreover, the use of the term's first, second, etc. does not denote any order of importance, but rather the term's first, second, etc. are used to distinguish one element from another. Furthermore, the use of the terms a, an, etc. do not denote a limitation of quantity, but rather denote the presence of at least one of the referenced items.

What is claimed is:

1. An electron emitter assembly, comprising:
a laser configured to emit a first light beam;
a lens assembly configured to receive the first light beam, the lens assembly configured to adjust a size of the first light beam between a first predetermined size and a second predetermined size larger than the first predetermined size, the lens assembly emitting the first light beam toward a photo-cathode;
the photo-cathode being configured to emit a first electron beam having a third predetermined size when the first light beam having the first predetermined size contacts the photo-cathode, the photo-cathode being further configured to emit a second electron beam having a fourth predetermined size when the first light beam having the second predetermined size contacts the photo-cathode; and
an anode configured to receive the first and second electrons beams from the photo-cathode.

2. The electron emitter assembly of claim 1, wherein the anode is configured to emit a first x-ray beam having a fifth predetermined size in response to receiving the first electron beam, the anode being further configured to emit a second x-ray beam having a sixth predetermined size in response to receiving the second electron beam, the sixth predetermined size being larger than the fifth predetermined size.

3. The electron emitter assembly of claim 1, wherein the lens assembly extends along a first axis, the lens assembly comprising a diverging lens and a converging lens, the converging lens configured to receive the first light beam from the diverging lens, the converging lens configured to move along the first axis to adjust a size of the first light beam between the first predetermined size and the second predetermined size larger than the first predetermined size.

4. The electron emitter assembly of claim 1, wherein the photo-cathode is a layer constructed from one or more of copper, silver, gold, magnesium, yttrium, calcium, indium gallium arsenide, gallium arsenide, gallium arsenide phosphide, gallium aluminum arsenide, cadmium telluride, cesium telluride, or sodium potassium antimonide.

5. An electron emitter assembly, comprising:
first and second laser diodes configured to emit first and second light beams, respectively, toward first and second regions of a photo-cathode, respectively;
the photo-cathode configured to emit a first electron beam having a first predetermined size when the photo-cathode receives the first light beam from the first laser diode, the photo-cathode further configured to emit a second electron beam having a second predetermined size larger than the first predetermined size when the photo-cathode simultaneously receives the first and second light beams from the first and second laser diodes; and
an anode configured to receive the first and second electron beams from the photo-cathode.

6. The electron emitter assembly of claim 5, wherein the anode is configured to emit a first x-ray beam having a third predetermined size in response to receiving the first electron beam, the anode being further configured to emit a second x-ray beam having a fourth predetermined size in response to simultaneously receiving the second electron beam, the fourth predetermined size being larger than the third predetermined size.

7. The electron emitter assembly of claim 5, wherein the photo-cathode is a layer constructed from one or more of copper, silver, gold, magnesium, yttrium, calcium, indium gallium arsenide, gallium arsenide, gallium arsenide phosphide, gallium aluminum arsenide, cadmium telluride, cesium telluride, or sodium potassium antimonide.

8. A method for adjusting a size of an electron beam, comprising:
adjusting a size of a first laser light beam utilizing a lens assembly between a first predetermined size and a second predetermined size greater than the first predetermined size that is emitted toward a photo-cathode;
emitting a first electron beam having a third predetermined size from the photo-cathode toward an anode in response to the photo-cathode receiving the first laser light beam having the first predetermined size; and
emitting a second electron beam having a fourth predetermined size greater than the third predetermined size from the photo-cathode toward the anode in response to the photo-cathode receiving the first laser light beam having the second predetermined size.

9. A method for adjusting a size of an electron beam, comprising:
adjusting a size of a first light beam between a first predetermined size and a second predetermined size greater than the first predetermined size that is emitted toward a photo-cathode;
emitting a first electron beam having a third predetermined size from the photo-cathode toward an anode in response to the photo-cathode receiving the first light beam having the first predetermined size;
emitting a second electron beam having a fourth predetermined size greater than the third predetermined size from the photo-cathode toward the anode in response to the photo-cathode receiving the first light beam having the second predetermined size;

emitting a first x-ray beam having a fifth predetermined size in response to the anode receiving the first electron beam; and emitting a second x-ray beam having a sixth predetermined size in response to the anode receiving the second electron beam, the sixth predetermined size being larger than the fifth predetermined size.

10. A method for adjusting a size of an electron beam, comprising:

emitting a first laser light beam having a first predetermined size towards a photo-cathode;

emitting a first electron beam having a second predetermined size from the photo-cathode toward an anode in response to the photo-cathode receiving the first laser light beam;

emitting both a second laser light beam having a third predetermined size and the first laser light beam toward the photo-cathode; and emitting a second electron beam having a fourth predetermined size from the photo-cathode toward the anode in response to the photo-cathode receiving the first and second laser light beams, the fourth predetermined size being greater than the second predetermined size.

11. A method for adjusting a size of an electron beam, comprising:

emitting a first light beam having a first predetermined size towards a photo-cathode;

emitting a first electron beam having a second predetermined size from the photo-cathode toward an anode in response to the photo-cathode receiving the first light beam;

emitting both a second light beam having a third predetermined size and the first light beam toward the photo-cathode;

emitting a second electron beam having a fourth predetermined size from the photo-cathode toward the anode in response to the photo-cathode receiving the first and second light beams, the fourth predetermined size being greater than the second predetermined size;

emitting a first x-ray beam having a fifth predetermined size in response to the anode receiving the first electron beam; and emitting a second x-ray beam having a sixth predetermined size in response to the anode receiving the second electron beam, the sixth predetermined size being greater than the fifth predetermined size.

* * * * *